(12) United States Patent
Weaver et al.

(10) Patent No.: US 10,223,499 B2
(45) Date of Patent: Mar. 5, 2019

(54) METHOD AND APPARATUS FOR IDENTIFICATION OF BIOMOLECULES

(71) Applicant: GENFORMATIC, LLC, Austin, TX (US)

(72) Inventors: Daniel B. Weaver, Austin, TX (US); Justin T. Reese, Milledgeville, GA (US)

(73) Assignee: GENFORMATIC, LLC, Austin, TX (US)

( * ) Notice: Subject to any disclaimer, the term of this patent is extended or adjusted under 35 U.S.C. 154(b) by 131 days.

(21) Appl. No.: 14/935,331

(22) Filed: Nov. 6, 2015

(65) Prior Publication Data

US 2016/0063180 A1 Mar. 3, 2016

Related U.S. Application Data

(63) Continuation of application No. 13/789,668, filed on Mar. 7, 2013, now abandoned.
(Continued)

(51) Int. Cl.
*G06F 19/00* (2018.01)
*G06F 19/22* (2011.01)
(Continued)

(52) U.S. Cl.
CPC ......... *G06F 19/22* (2013.01); *G01N 33/6803* (2013.01); *G06F 19/12* (2013.01); *G06F 19/18* (2013.01); *G06F 19/24* (2013.01)

(58) Field of Classification Search
CPC .......... G06F 19/16; G06F 19/22; G06F 19/12; G06F 19/18; G06F 19/24; G06F 19/28; G06F 19/26; G06F 19/702; G06F 19/20; G06F 19/3431; G06F 19/3437; G06F 19/345; G06F 19/14; G06F 19/706; G06F 19/3443; G06F 19/70; G06F 17/16; G06F 17/18; G06F 17/30312; G06F 17/3033; G06F 17/30386; G06F 17/30548; G06F 17/30598; G06F 17/30864;
(Continued)

(56) References Cited

U.S. PATENT DOCUMENTS 6,188,965 B1 * 2/2001 Mayo ...................... C07K 1/00
   702/27
2003/0022200 A1  1/2003 Vissing et al.
(Continued)

*Primary Examiner* — Mary K Zeman
(74) *Attorney, Agent, or Firm* — Polsinelli PC

(57) ABSTRACT

The present disclosure presents methods, systems, and devices for identifying new molecules directly from biological sequence information, with at least one of a desired bioactivity profile, functional attribute, biochemical reactivity, biological impact, pharmacological characteristic or therapeutic effect. The present disclosure further includes analyzing, at the processor, data features of biological sequence information and other data sources, including a feature-definition set by processing, using one or more bioinformatic techniques, computational algorithms, or methods of statistical machine learning, data sources relating to biological or chemical molecules, including biomolecules, including but not limited to peptides, having desired physical or chemical characteristics, bioactivities, functional attributes, biological impacts, pharmacologic properties or therapeutic effects.

6 Claims, 2 Drawing Sheets

Related U.S. Application Data

(60) Provisional application No. 61/608,084, filed on Mar. 7, 2012.

(51) Int. Cl.
  *G01N 33/68* (2006.01)
  *G06F 19/12* (2011.01)
  *G06F 19/18* (2011.01)
  *G06F 19/24* (2011.01)

(58) Field of Classification Search
  CPC ............. G06F 17/30867; G06F 19/322; G06F 19/325; G06F 19/326; G06F 19/3406; G06F 19/3456; G06F 19/3475; G06F 19/3481; G06F 19/363; G06F 19/366; G06F 19/701; G06F 19/705; G06F 19/707; G06F 19/708; G06F 21/6227; G06F 21/6245; G06F 3/0481; G06F 3/0482; G06F 3/04847; G06N 3/0445; G06N 3/082; G06N 5/04; G06N 7/005; G06N 99/005; G06N 3/0472; G06N 3/08; G06N 5/048; G01N 33/6803; G01N 2500/00; G01N 33/68; G01N 30/88; G06Q 10/10; G06Q 30/02; G06Q 30/0631; G06Q 50/22; G06T 15/205; G06T 17/10; G06T 17/20; G06T 2210/16; G09B 19/00; G09B 23/28; G09B 5/12
  See application file for complete search history.

(56) References Cited

U.S. PATENT DOCUMENTS

| | | | |
|---|---|---|---|
| 2007/0197773 A1* | 8/2007 | Stephanopoulos | C07K 7/08 530/324 |
| 2007/0271604 A1 | 11/2007 | Webster et al. | |
| 2008/0050357 A1* | 2/2008 | Gustafsson | C07K 16/1027 424/130.1 |
| 2008/0220990 A1* | 9/2008 | Fox | C40B 30/02 506/40 |
| 2009/0191607 A1* | 7/2009 | Baker | C12N 9/88 435/195 |
| 2011/0280466 A1 | 11/2011 | Cho et al. | |
| 2011/0288826 A1* | 11/2011 | Breaker | G06F 19/16 703/2 |
| 2013/0053541 A1 | 2/2013 | Shankar et al. | |

\* cited by examiner

METHOD AND APPARATUS FOR IDENTIFICATION OF BIOMOLECULES

CROSS-REFERENCE TO RELATED APPLICATION

This application is a continuation of U.S. application Ser. No. 13/789,668, filed Mar. 7, 2013, which claims the benefit of the U.S. Provisional Application No. 61/608,084, filed Mar. 7, 2012, the contents of which are expressly incorporated by reference herein.

FIELD

The present disclosure relates to securing and/or comparing genomic data. Specifically, encryption of genomic data is presented. Additionally, a comparison technique is presented to determine similarities between two sets of genomic data.

BACKGROUND

Genomic data has become increasingly easy and cost effective to produce and genomic data is accumulating with considerable velocity. At the same time, the medical, social and personal utility of genomic information is expanding, revealing new and potentially transformative applications of genomic technology.

BRIEF DESCRIPTION OF THE DRAWINGS

Implementations of the present technology will now be described, by way of example only, with reference to the attached figures, wherein.

DETAILED DESCRIPTION

Figure 1:
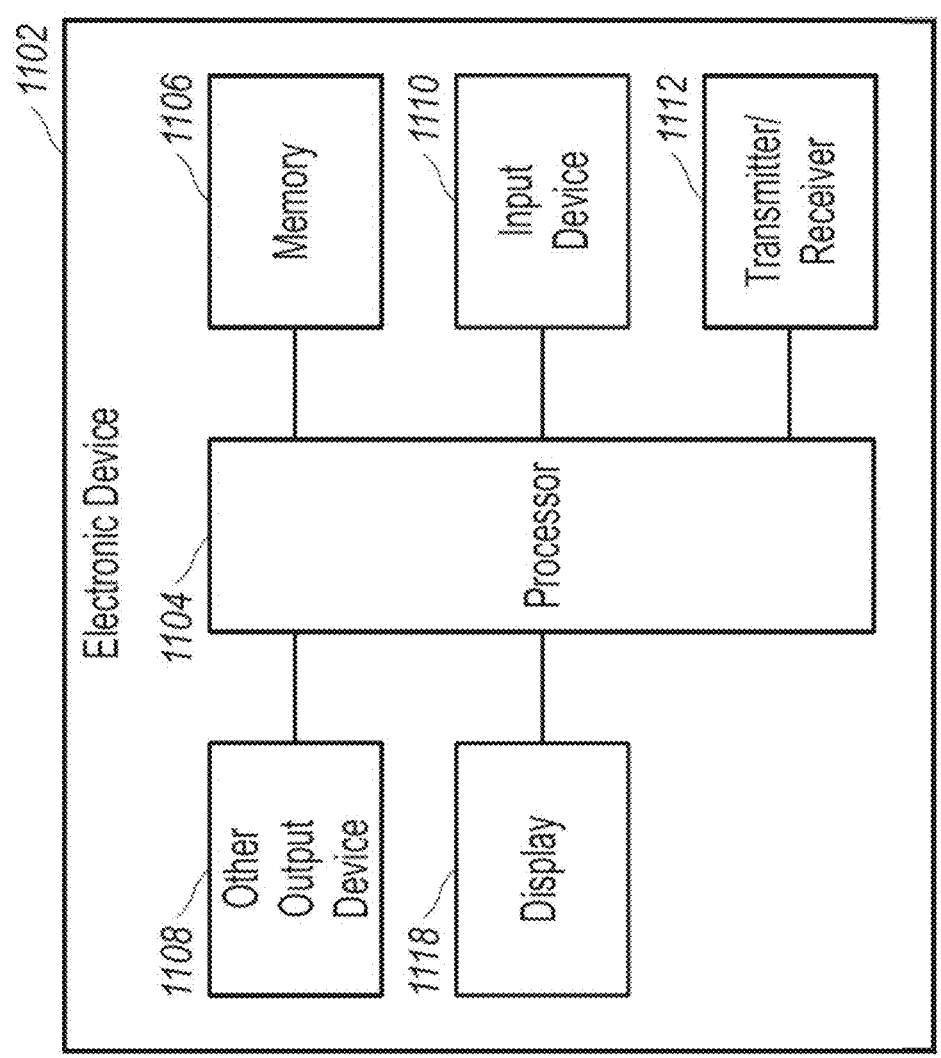
FIG. 1 illustrates an example of an electronic device according to an example implementation.

For simplicity and clarity of illustration, where appropriate, reference numerals have been repeated among the different figures to indicate corresponding or analogous elements. In addition, numerous specific details are set forth in order to provide a thorough understanding of the implementations described herein. However, those of ordinary skill in the art will understand that the implementations described herein can be practiced without these specific details. In other instances, methods, procedures and components have not been described in detail so as not to obscure the related relevant feature being described. Also, the description is not to be considered as limiting the scope of the implementations described herein.

By way of example, one may implement the claims to bioinformatically and computationally explore, via latent class analysis, a set of peptides with known antimicrobial activity, and another set of peptides with similar molecular weight and amino acid composition. The program and processor will use principals of latent class analysis, especially Bayesian inference, to identify those data parameters that characterize the group exhibiting the property of interest (antimicrobial activity) and distinguishes the lead drug molecules from seemingly similar peptides lacking the desired functionality.

Next, the data parameters distinguishing the biomolecules with the desired activity from other peptides that lack the desired activity are applied as search criteria to explore new biological data generated, for example, by a newly sequenced genome. Candidate molecules exhibiting the data parameters associated with the desired bioactivity profile are identified, and then subsequently synthesized and tested in a simple bioassay.

The peptides in the candidate bioactivity class with validated bioactivity are passed up to further evaluation for drug safety and efficacy, while those failing the bioactivity test are used to further refine and improve the latent class analysis used to separate molecules with and without the desired performance characteristic.

Pharmacological research and development, and the delivery of new drugs to market is hampered the by cost, complexity and time delays in identifying new drug candidates, testing lead drug compounds, and improving the overall efficiency and efficacy of drug research and development. Better methods to identify promising new drug molecules, screen lead compounds for efficacy and streamline the R&D pipeline are urgently needed. Breakthrough innovation is important to Pharmaceutical industry worldwide.

An integrated bioinformatic drug molecule prediction method and wet-lab screening and efficacy validation method is presented herein that uses statistical machine learning to iteratively and continuously improve algorithmic drug candidate identification performance, based upon the evidence of desired lead compound efficacy or failure generated by simple bioassay validation or rejection of predicted new drug molecule bioactivity.

The present disclosure includes a method for searching available data, including but not limited to biological sequence data, especially genome sequence or transcriptome sequence information. The present disclosure uses sequence or other data features of peptides or other biomolecules with known attributes as criteria, to identify new candidate molecules with probable bioactivity.

Intrinsic to this concept is the subsequent use of a bioassay to confirm or reject the predicted bioactivity of new candidate molecules. Thus the results of the bioassay may be applied to iteratively refine and improve the bioinformatic data correlation or search criteria to improve its specificity and sensitivity in identifying promising new drug compounds with pre-specified desirable properties.

One, but by no means the only, novelty in this invention lies in the integration of the predicted compound screening and bioactivity testing results to "teach" the bioinformatic algorithm to modify the search criteria to increase the likelihood of identifying novel proteins/peptides or other biomolecules with desired biological activity and reduce the chances of flagging compounds that lack the desired drug profile.

The present disclosure can provide a computer processor or server, in any number of different architectures and configurations, implementing methods to "learn" how to better identify molecules with selected attributes in a targeted bioinformatic search of large datasets—the data consisting in part of the enormous streams of new information flowing from sequencing thousands of new microbial genomes and hundreds of new plant and animal genomes each year, and the learning imparted by the concomitant bioactivity assay that constantly provides feedback on the predicted compounds that actually exhibit the desired functionality.

New genomes being sequenced each year may harbor thousands of novel polypeptide sequences, expressed by the organism for one purpose but potentially useful in new environmental and physiological contexts. Venom protein constituents in one organism may prove to be medicines or helpful compounds in a variety of alternative applications.

The method as presented herein can be adaptable to any gene or gene product that can be used in a functional screening bioassay. The bioinformatic search can be based on measurable attributes of the gene/gene product that could include, but not be limited to, physicochemical properties of amino acids as specific locations within the peptide sequence, amino acid biases or paucities within the total sequence, specific patterns or motifs conserved among peptides of specific sizes, overall predicted protein sizes, predicted, cellular targeting signals, etc.

An example of this approach would be the specific mining of genomic data for genes encoding small peptides (typically less than 50 amino acids) that have antimicrobial activity. The small antimicrobial peptide approach is presented as a proof-of-concept strategy; however, it is envisioned that this technique would be applicable to iterative mining-bioassay-mining-bioassay activities of any gene product for which a bioassay could be developed and functional synthetic copies of the gene product could be produced in a facile manner (i.e. either direct synthesis of peptides, rapid cDNA cloning and expression of the gene product; or whole gene synthesis followed by gene product expression).

The algorithm will first identify substantially all regions of a given genome that could encode for peptides of a given size, followed by specific detection of sequence motifs or amino acids at positions within the peptide that are conserved for known classes of antimicrobial peptides. Next predictive peptide folding can be performed on selected targets to determine if steric interactions allow folding structures presumed to be necessary for a specific bioactive class of peptides/proteins. The subset of putative antimicrobial peptides can then be scored based on their fit to the predictive models and synthetic small peptides will be synthesized and used in antimicrobial bioassays to characterize biological activity. Presence of biological activity, and quantitative comparison of activities will then be used to adapt mining algorithms for subsequent rounds of discovery form genomes of other organisms.

The present disclosure is not limited to the specific discovery of novel peptides (defined here as something less than 50 amino acids), because it can be applied to any protein for which iterative cycles of (mining-synthesis-bioassay)n can be performed, the description of the process will focus on the use of this strategy for small peptides with desired biological activity.

It is envisioned, and ever increasingly demonstrated, that biologically-based molecules discovered through bioinformatics mining can be useful in human health (especially in treating infections), agriculture (with applications as pesticides, herbicides and antimicrobials) influencing crop plant and animal performance, energy production (enabling or improving biofuel production through their biological activity) and other aspects of human endeavor, including detoxification of polluted environments.

Several definitions that apply throughout this disclosure will now be presented.

An electronic device as described herein is a device which includes a processor and memory. The memory can be either transitory or non-transitory as described below. Examples of electronic devices include desktops, laptops, servers, tablets, smartphones and personal digital assistants.

A feature-definition set can be one or more of the following genome sequences of one or more organisms or a transcriptome sequence of one or more organisms.

A biomolecule as used herein can include at least a biological sequence data encoding to biological or biochemical molecules.

A bioactivity profile can include one or more of the following chemistry, bioactivity, functional attribute, biological impact, pharmacology or therapeutic effect.

The feature-detection set can include the biological sequences of a second or subsequent organism or group of organisms.

The present disclosure generally concerns identification of biomolecules.

As indicated above, the technology can be implemented on one or more electronic devices. The electronic devices can be a server, a computer, a laptop, a desktop, a tablet, a smartphone, a handheld device, a personal data assistant, or the other device which includes one or more processors. The electronic device can further include memory, which can be non-transitory memory. Examples within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other examples of the disclosure may be practiced in network computing environments with many types of computer system configurations, including personal computers, handheld devices, multi-processor systems, microprocessor-based or programmable consumer electronics, network PCs, minicomputers, mainframe computers, and the like. Examples may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

FIG. 1 illustrates an example of an electronic device 1102 according to an example implementation. As illustrated, the electronic device includes a processor 1104. The processor can be communicatively coupled to one or more of the components of the electronic device 1102. For example, the processor is communicatively coupled to memory 1106. The memory 1106 can be RAM, ROM, flash or any other type of memory including transitory and non-transitory memory. The processor 1104 can be communicatively coupled to an input device 1110 that is configured to enable an operator to input data to the electronic device 1102. The input device can be a keyboard, touchscreen, navigation tool or other device that is configured to provide data to the electronic device 1102 for data input. The processor 1104 can be further communicatively coupled to a transmitter/receiver 1112. The transmitter/receiver 1112 can include one or more transmitters/receivers. The transmitters enable the device to transmit data externally to the device, and the receivers enable the device to receive data from a source external to the device. In at least one embodiment, the transmitter/receiver can be a single device and in other embodiments, they can be separate devices. The processor 1104 can further be communicatively coupled to a display 1118 for displaying of data to an operator. Furthermore, the processor 1104 can further be coupled to at least one other output device 1108. These are other devices which enable the electronic device 1102 to output data to an operator.

The electronic device 1102 can be anyone of the above described devices. In some embodiments, the electronic device 1102 can include only some of the components illustrated in FIG. 1. Additionally, the electronic device 1102 can include additional components which are not illustrated.

The electronic device 1102 can be configured such that the processor 1104 is capable and/or configured to execute the steps as recited in the methods presented herein. The memory 1106 is configured to store the data. Furthermore, the transmitter 1112 is configured to transmit data from the electronic device 1102.

Figure 2:
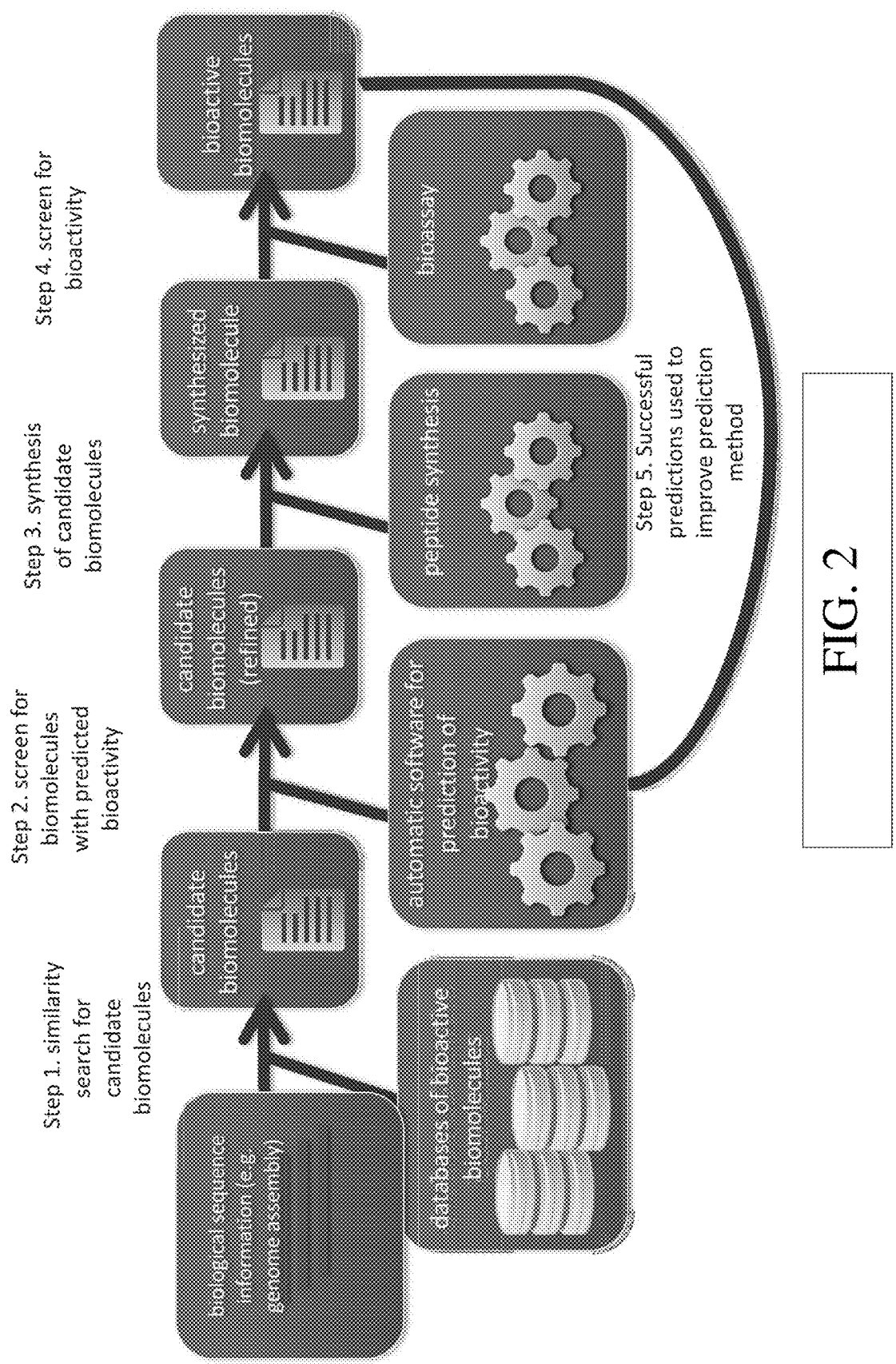
FIG. 2 illustrates a flow chart of an example method according to an example implementation.

As illustrated in FIG. 2, the present disclosure also presents a method of identifying, on an electronic device including a processor and memory, new molecules directly from biological sequence information, with at least one of a desired bioactivity profile, functional attribute, biochemical reactivity, biological impact, pharmacological characteristic or therapeutic effect. The method can include analyzing, at the processor, data features of biological sequence information and other data sources, including a feature-definition set by processing, using one or more bioinformatic techniques, computational algorithms, or methods of statistical machine learning, data sources relating to biological or chemical molecules, including biomolecules, including but not limited to peptides, having desired physical or chemical characteristics, bioactivities, functional attributes, biological impacts, pharmacologic properties or therapeutic effects.

The method can further include deriving, at the processor, a set of data features, including but not limited to biological sequence features, using methods of statistical machine learning, computational biology or bioinformatics, that distinguish biological sequences encoding to peptides or other biomolecules, or the peptides or other biomolecules with the desired bioactivity profile from biological sequences encoding to peptides or other biomolecules that lack the desired bioactivity profile. In another embodiment, the can further include deriving, at the processor, a set of data features, using methods of statistical machine learning, computational biology or bioinformatics, that distinguish, define or are shared by sets of biological sequences encoding to peptides or other biomolecules with the desired bioactivity profile.

In a further step, the method can include searching, at the processor, a feature-detection set for biological sequence features that are the same as or similar to the sequence features distinguishing, defining or shared by sequences encoding, regulating or relating to peptides or other biomolecules with the desired bioactivity profile. In still a further step, the method can include compiling, at the processor, a list of the shared feature sequences discovered in the feature-detection genome set encoding, regulating or relating to novel peptides or other biomolecules predicted to have the desired bioactivity profile.

Still further, the method can include producing, at the biomolecule synthesis system, the predicted biomolecules discovered in the feature-detection set using standard procedures of molecular synthesis. The procedures of molecular synthesis include at least one of in-vitro chemical synthesis, recombinant viral, bacterial, fungal, insect, protist, cell-culture, fosmid, cosmid or plasmid cloning and expression vectors, plants biomolecule cloning, expression and synthesis systems, synthetic biological organisms for biomolecule production, extraction or harvest of biomolecules from the organisms in which they are naturally present, or other natural or engineered expression and production systems for biomolecules. Additionally, the method can include testing, at the bioassay evaluation device, the predicted biomolecules using an appropriate bioassay designed to assess the actual bioactivity profile of the produced biomolecules.

The method can include a further step of compiling, at the processor, a list of the predicted biomolecules that exhibit the desired bioactivity profile (hereafter "validated biomolecules") and a list of biomolecules that lack the desired bioactivity profile (hereafter "rejected biomolecules"). The method can further include refining, at the processor, the shared feature sequences that are associated with the validated biomolecules, but are not associated with the rejected biomolecules by performing one or more additional iterations of the following steps: encoding, using one or more bioinformatic techniques, computational algorithms, or methods of statistical machine learning, to biological or biochemical molecules, including but limited to peptides, having desired physical or chemical characteristics, bioactivities, functional attributes, biological impacts, pharmacologic properties or therapeutic effects, and deriving a set of biological data features, using methods of statistical machine learning, that distinguish, define or are shared by peptides or other biomolecules, or sets of biological sequences encoding to peptides or other biomolecules, with the desired bioactivity profile.

The methods of statistical machine learning, computational biology or bioinformatics comprise at least one of an association rule learning, principal component analysis, latent class analysis, latent class prediction by Bayesian inference, support vector machines, semi-supervised learning, reinforcement learning, directed acyclic graphical models, distance-metric and similarity learning, artificial neural networks and hierarchical feature detection and representation.

The other data sources can include at least one of chemical structure data, number of hydrogen bond donors or acceptors, molecular weight, number of rotational bonds, pH data, pKa data, pharmacokinetic data, pharmacodynamic data, hydrophobicity, lipophilicity, membrane permeability, diffusion coefficient, physiological transport dynamics, cellular localization data, absorption data, number of side chains, structural motif data, number of disulfide bonds, number or spatial arrangement of intramolecular bonds, secondary or tertiary structure, three dimensional shape or conformation, protein-protein interaction structure or potential, potential polymerization or interaction potential, P-450 enzyme interaction data, metabolic data, excretion or clearance data, liver toxicity data, Ames test data, drug persistence data, mammalian LD50 data, inter-molecular conjugation data, molecular cyclization data, biomolecular helix, sheet, strand, loop or turn data, electro-chemical data, ionization potential, water solvation data, oral bioavailability data, polar surface area data, drug safety data, drug efficacy data, small molecule analog data, kinase, G-protein, cellular receptor, secretory or signaling molecule, hormone, antibody or antigen or other moiety or species analog, agonist, antagonist or mimetic data, gene expression data, protein expression data, or drug target epitope data.

The method can further include compiling, at the processor, a revised shared feature sequence data. Still further the method can include searching, at the processor, the biological sequence information of the feature detection set, or a new feature detection set which includes some additional biological sequence information from one or more organisms using the revised shared feature sequence data. The method can further include compiling, at the processor, a new or improved predicted biomolecule list with associated sequence features.

The method can further include one or more iterations of one or more of the following steps: the production of the predicted biomolecules by producing, at the biomolecule synthesis system, the predicted biomolecules discovered in the feature-detection set using standard procedures of molecular synthesis; the testing of the new or improved predicted biomolecules by testing, at the bioassay evaluation device, the predicted biomolecules using an appropriate bioassay designed to assess the actual bioactivity profile of the produced biomolecules; the compilation of a new or revised list of validated and rejected biomolecules, as compiling, at the processor, a list of the predicted biomolecules that exhibit the validated biomolecules and a list of biomolecules that lack the rejected biomolecules; refining, at the processor, the shared feature sequences that are associated with the validated biomolecules, but are not associated with the rejected biomolecules by performing one or more additional iterations of the following steps: encoding, using one or more bioinformatic techniques, computational algorithms, or methods of statistical machine learning, to biological or biochemical molecules, including but limited to peptides, having desired physical or chemical characteristics, bioactivities, functional attributes, biological impacts, pharmacologic properties or therapeutic effects, and deriving a set of biological data features, using methods of statistical machine learning, that distinguish, define or are shared by peptides or other biomolecules, or sets of biological sequences encoding to peptides or other biomolecules, with the desired bioactivity profile; and compiling, at the processor, a revised shared feature sequence data.

An electronic device 1102 can be configured to identify new molecules directly from biological sequence information, with at least one of a desired bioactivity profile, functional attribute, biochemical reactivity, biological impact, pharmacological characteristic or therapeutic effect. The electronic device 1102 can be one such as the one illustrated in FIG. 1. The electronic device can include a processor and a memory communicatively coupled to the processor. The memory can configured to store instructions to cause the processor to execute the steps as described above. For example, the processor can analyze data features of biological sequence information and other data sources, including a feature-definition set by processing, using one or more bioinformatic techniques, computational algorithms, or methods of statistical machine learning, data sources relating to biological or chemical molecules, including biomolecules, including but not limited to peptides, having desired physical or chemical characteristics, bioactivities, functional attributes, biological impacts, pharmacologic properties or therapeutic effects.

The electronic device can be further configured to execute the steps as described above in regards to the method.

The various embodiments described above are provided by way of illustration only and should not be construed to limit the scope of the disclosure. Those skilled in the art will readily recognize various modifications and changes that may be made to the principles described herein without following the example embodiments and applications illustrated and described herein, and without departing from the scope of the disclosure.

What is claimed is:

1. A method of identifying, on an electronic device comprising a processor and a memory, directly from biological sequence information, biomolecules having a desired bioactivity, the method comprising:
   (a) processing, at the processor, data sources relating to a desired bioactivity, including biological sequence information, using Bayesian inference;
   (b) analyzing, at the processor, using Bayesian inference, structural features of the data from step (a), to derive a computational algorithm that identifies a first set of structural features that distinguish the known biomolecules having the desired bioactivity (each a "distinguishing structural feature"), wherein the distinguishing structural features of the first set include molecular weight, conserved sequence motifs, and conserved amino acids, and optionally include number of hydrogen bond donors and/or acceptors, number of rotational bonds, hydrophobicity, lipophilicity, membrane permeability, diffusion coefficient, cellular localization data, number of side chains, structural motif data, number of disulfide bonds, number and/or spatial arrangement of intramolecular bonds, secondary structure, tertiary structure, three dimensional conformation, protein-protein interaction potential, or polymerization potential;
   (c) deriving, at the processor, an improved set of distinguishing structural features that, as compared to the first set of distinguishing structural features, more accurately distinguishes the known biomolecules having the desired bioactivity from known biomolecules lacking the desired bioactivity by:
      (i) using the algorithm from step (b) to search, at the processor, genome sequence data from databases for biological sequences encoding biomolecules comprising one or more distinguishing structural feature of the first set (each biomolecule "a candidate biomolecule"), wherein the algorithm identifies substantially all regions of a given genome that could encode for biomolecule of a given molecular weight and detects conversed sequence motifs and/or conserved amino acids, and any optional structural feature, and (ii) compiling from the genome sequence data, at the processor, a list of candidate biomolecules based on step (c)(i);

(iii) producing, at a biomolecule synthesis system, a random subset of the candidate biomolecules;

(iv) measuring, at a bioassay evaluation device, the level of the desired bioactivity of the synthesized candidate biomolecules and then scoring the candidate biomolecules based on their relative performance;

(v) determining, at the processor, using Bayesian inference, the structural features that distinguish candidate biomolecules having the desired bioactivity from candidate biomolecules lacking the desired bioactivity, based upon the results of step (c)(iv) and using this information to modify the algorithm of step (c)(i); and (vi) repeating steps (i) to (v) at least once, at the processor, to further refine the derivation of structural features that distinguish candidate biomolecules having the desired bioactivity from candidate biomolecules lacking the desired bioactivity, wherein upon the final repetition of step (c), the candidate biomolecules compiled in step (c)(ii) identify biomolecules having the desired bioactivity.

2. The method as in claim 1, wherein the biological sequences are selected from the group consisting of DNA nucleotide sequences, RNA nucleotide sequences, amino acid sequences, chemically modified DNA nucleotide sequences, biologically modified DNA nucleotide sequences, chemically modified RNA nucleotide sequences, biologically modified RNA nucleotide sequences, chemically modified amino acid sequences, biologically modified amino acid sequences, chemically modified protein sequences, and biologically modified protein sequences.

3. The method as in claim 1, wherein the desired bioactivity is an effect selected from the group consisting of biochemical, biophysical, pharmacological, therapeutic, antimicrobial, cytotoxic, antitumor, antiproliferative, and antineoplastic.

4. The method as in claim 1, wherein the structural features are a primary, secondary or tertiary structure of an amino acid sequence translated from a RNA nucleotide sequence, and the amino acid sequence is computed by virtual translation of a RNA nucleotide sequence by a processor or device.

5. The method as in claim 1, wherein the structural features are a primary, secondary, or tertiary structure of an amino acid sequence translated from a RNA nucleotide sequence by a biological molecule.

6. The method as in claim 1, wherein the structural features of the known biomolecules characterized as having the desired bioactivity are associated with a chemical, physical, biological, pharmacological or clinical functionality of an amino acid sequence, a RNA sequence, or a DNA sequence constituting or coding for a molecule with an anti-bacterial, anti-viral, anti-fungal, anti-parasitic, or anti-pathogen activity.

* * * * *